United States Patent
Daum et al.

(10) Patent No.: US 6,231,513 B1
(45) Date of Patent: May 15, 2001

(54) CONTRAST AGENT FOR ULTRASONIC IMAGING

(75) Inventors: Wolfgang Daum, Schwerin; Wolfgang Kloess, Lübeck, both of (DE)

(73) Assignee: Daum GmbH, Schwerin (DE)

(*) Notice: Subject to any disclaimer, the term of this patent is extended or adjusted under 35 U.S.C. 154(b) by 0 days.

(21) Appl. No.: 09/172,387

(22) Filed: Oct. 14, 1998

(51) Int. Cl.⁷ .................................................. A61B 8/00
(52) U.S. Cl. .................................................. 600/458
(58) Field of Search .................................. 600/458, 459, 600/431, 420; 604/24, 26, 509; 75/414; 424/9.52

(56) References Cited

U.S. PATENT DOCUMENTS

| | | |
|---|---|---|
| 3,640,271 | 2/1972 | Horton . |
| 5,163,421 | 11/1992 | Bernstein et al. . |
| 5,236,693 * | 8/1993 | Lee ............................................. 424/9 |
| 5,249,579 | 10/1993 | Hobbs et al. . |
| 5,599,296 * | 2/1997 | Spears ....................................... 604/26 |
| 5,833,613 * | 11/1998 | Averkiou et al. ....................... 600/440 |
| 5,869,538 * | 2/1999 | Van Liew et al. ...................... 514/743 |

FOREIGN PATENT DOCUMENTS 29 46 662 A1   5/1981   (DE) .

* cited by examiner

*Primary Examiner*—Marvin M. Lateef
*Assistant Examiner*—Maulin Patel
(74) *Attorney, Agent, or Firm*—Altera Law Group, LLC

(57) ABSTRACT

The present invention is directed to apparatuses and methods for determining blood flow characteristics and imaging interior surface contours within vessel walls. In a preferred embodiment, the method of the invention includes a hollow tubular lumen having a proximal end and distal end wherein the distal end includes a microbubble forming arrangement for forming microbubbles when a gas is passed through the distal end of the hollow tube.

18 Claims, 4 Drawing Sheets

ID: 4dffcddb-a9a6-48b5-bdf7-447538596f3b
CONTRAST AGENT FOR ULTRASONIC IMAGING

FIELD OF THE INVENTION

The present invention is directed to the field of diagnostic imaging. Specifically, the invention provides apparatuses and methods for delivery of a gaseous contrast media to a fluid containing medium for detection using ultrasonic imaging.

BACKGROUND OF THE INVENTION

The injection of minute gas bubbles into a patient's bloodstream for measuring pressure and flow characteristics of blood are disclosed in, for example, DE 29 46 662 A1 and U.S. Pat. No. 3,640,271. In German patent application DE 29 46 662 A1, the velocity of gas bubbles in the bloodstream is measured using ultrasound techniques and from this measurement, the velocity of the bloodstream is determined.

In U.S. Pat. No. 3,640,271, bubbles are sequentially injected into the bloodstream and the velocity of the bubbles is measured using ultrasound imaging procedures. The velocity of blood flow is determined by calculations using equations disclosed in the patent. The bubbles are formed by agitating a container holding a blood compatible solution, such as a saline solution, and a blood compatible gas. The bubbles are withdrawn from the container using a hypodermic needle having a filter such that only bubbles of less than 0.0025 cm are drawn into the syringe. The collected bubbles are then injected into the bloodstream and flow characteristics are measured using sound wave technology including Doppler and ultrasonic techniques.

U.S. Pat. No. 5,249,579 discloses an apparatus for controlled injection of carbon dioxide gas into an animal's vascular system. The apparatus includes a mechanism for controlling the flow rate at which the gas is delivered so that the flow rate of the gas correlates to the flow rate of the blood in the animal's vascular system.

The injected $CO_2$ functions as a blood displacement media or a contrast medium.

U.S. Pat. No. 5,264,421 discloses an ultrasound structure having a wire for transmission of high power ultrasonic energy. The ultrasonic energy is applied to a vascular occlusion at a duration and intensity sufficient to substantially break up the occlusion and recanalize the patient's artery.

The entire disclosure of each of the references disclosed in the present specification are incorporated herein by reference.

SUMMARY OF THE INVENTION

The present invention is directed to apparatuses and methods for forming gas bubbles which can be used as a contrast agent. In one embodiment, the invention provides for delivery of gaseous microbubbles that can be detected by ultrasound techniques to study interior surface contours within vessel walls.

An apparatus of the invention provides for delivering a contrast agent into a patient's vessel. The apparatus comprises a tube having a lumen extending from a proximal end to a distal end of the tube and a microbubble forming arrangement at the distal end of the lumen. The microbubble forming arrangement includes microholes which cause formation of microbubbles when a gas is passed through the microbubble forming arrangement.

The tube of the apparatus can be, for example, a catheter, a needle, or other hollow structure. The microbubble forming arrangement can be a porous matrix having microholes or microchannels throughout or a membrane having microholes therethrough. According to the invention, a porous matrix can be of a material selected from ceramics, sintered alloys, sintered nickel-titanium, sintered polytetrafluoroethylene (PTFE), etc.

The invention also provides methods for delivering microbubbles to the interior surface of a vessel for imaging the vessel wall or determining fluid flow characteristics within the vessel.

DETAILED DESCRIPTION

Figure 1:
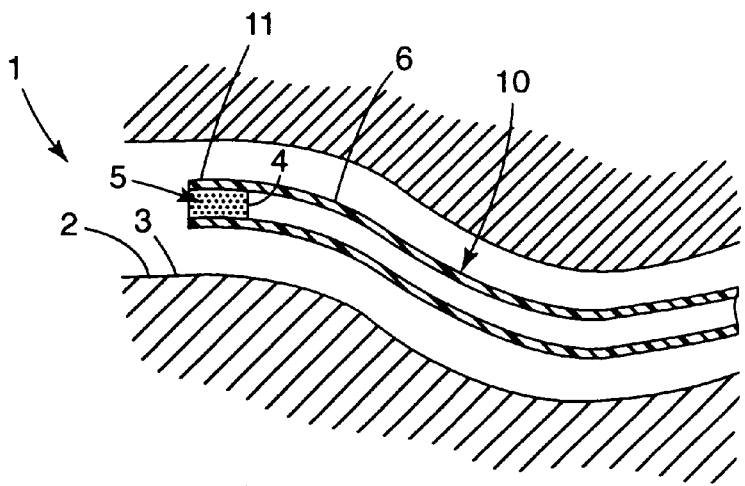
FIG. 1 is a longitudinal cross-section view of an apparatus for delivering a contrast agent into the lumen of a blood vessel according to the invention.

The use of contrast agents to image blood vessels, body cavities or caverns is known. Such contrast agents include, for example, iodinated materials, $CO_2$ gas or contrast agents including materials such as gadolinium for magnetic resonance imaging (MRI). In addition, contrast agents for detection using ultrasound imaging techniques are known. These imaging agents include gels containing very small bubbles. Many of these contrast agents, however, are expensive and may have side effects.

The present invention provides a safe and inexpensive alternative for formation of microbubbles using physiological or inert gasses such as, $CO_2$.

The apparatuses of the invention can be used to form microbubbles to study blood flow characteristics through a blood vessel. In another embodiment, microbubbles can be infused into a blood vessel to study surface contours of the interior walls of the vessel using ultrasound imaging techniques. It will be appreciated that, while the present specification describes the invention by reference to blood vessels, the apparatus and methods are suitable for use in other fluid containing structures of the body including, for example, the lymphatic system.

An apparatus of the invention includes a hollow tubular structure that can be passed into the vessel of a human or animal patient to a selected site. Suitable tubular structures which can be passed into the vessel of a patient include needles, catheters, or other tube structures. The hollow tube includes a proximal end and a distal end. The distal end is passed into the vessel.

At the proximal end, the tube includes a fitting for sealingly connecting a gas source to the hollow tube. A regulator for regulating rate of gas flow into the proximal end of the catheter can be attached to the gas source or along a line between the gas source and the proximal end of the catheter. Gasses used according to the invention are known and include any gas suitable for infusion into a human or animal patient. The gases can be provided from any known sources.

At the distal end, the tube includes a microbubble forming arrangement. As used herein, "a microbubble forming arrangement" is a structure that has a plurality of microholes which when a gas is passed through causes the gas to form numerous microbubbles as the gas passes out the distal end of the hollow tube into the patient's vessel.

Examples of microbubble forming arrangements include a multi-perforate membrane at the distal end of the tube or a porous matrix. As used herein, a "multi-perforate" membrane is a two dimensional material that includes microholes which cause formation of microbubbles when a gas is passed through the membrane. Typically, the multi-perforate membrane is attached at the distal end of the lumen of the tube. Examples of suitable materials for a multi-perforate membrane include known physiologically compatible materials such as polytetrafluoroethylene (PTFE), polyethylene, polyurethane, polypropylene, etc.

As used herein, a "porous matrix" refers to a three-dimensional structure which includes microholes or microchannels which cause formation of microbubbles when a gas is passed through. According to the invention, a porous matrix can be prepared from ceramic, sintered alloy, sintered nickel-titanium, sintered polytetrafluoroethylene (PTFE), etc.

According to the invention, a "microhole" is of a size sufficient to cause formation of microbubbles of a size sufficient for the particular procedure to be performed. A "microbubble" is a gas filled pocket of a size of about 1 $\mu$m to 500 $\mu$m. In typical embodiments for study of fluid flow characteristics through a vessel, microbubbles are about 10 $\mu$m to 50 $\mu$m. For embodiments used to study surface characteristics of the interior wall of a vessel, microbubbles of a size of 10 $\mu$m to 50 $\mu$m are suitable. In an alternative embodiment, microbubbles can be formed by passing the gas through a hollow tube and vibrating the tube with ultrasound waves to break the flow of gas into microbubbles.

According to the invention, "a vessel" includes blood vessels, lymph vessels or other tubular structures of a human or animal body for carrying fluid material. The apparatuses and methods of the invention are particularly suited for studying stenotic or other atheromatous materials which can cause occlusion of a blood vessel, using ultrasound imaging.

DETAILED DESCRIPTION OF THE ILLUSTRATED EMBODIMENT

Apparatuses and methods of the invention will now be described by reference to the illustrations. Referring to FIG. 1, a vessel 1 including an interior surface 2 surrounded by a vessel wall 3 is illustrated. Within the interior surface 2 of the vessel 1, there is an apparatus 10 for delivering a contrast agent according to the present invention. As illustrated, the apparatus 10 includes a hollow tube 6. The distal end 11 of apparatus 10 includes a microbubble forming arrangement 4. In the illustrated embodiment, the microbubble forming arrangement 4 is a porous matrix 5.

Figure 2:
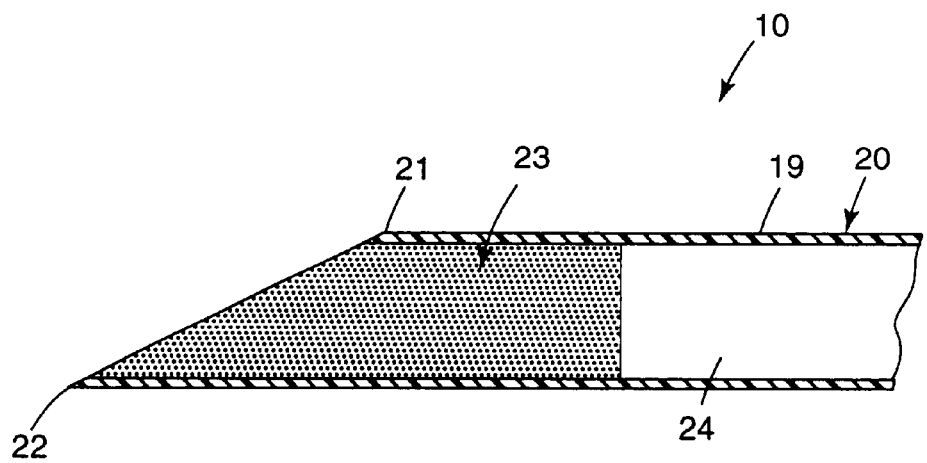
FIG. 2 is a longitudinal cross-section view of an alternative embodiment of the distal end of an apparatus for delivering a contrast agent according to the invention.

FIG. 2 illustrates a second embodiment of an apparatus 10 for delivering a contrast agent. According to this embodiment, hollow tube 19 is in the form of a piercing needle 20. At the distal end 21, the needle 20 has a needle tip 22 and a beveled porous matrix 23 within the lumen 24. Porous matrix 23 provides for formation of microbubbles when a gas is passed through lumen 24 of needle 20.

Figure 3D:
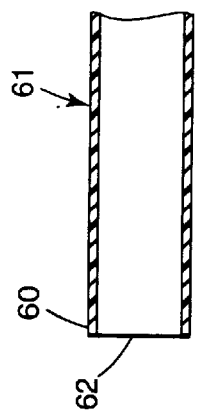
FIGS. 3a–3e illustrate four embodiments of an apparatus for delivering a contrast agent according to the invention having various types of microbubble forming arrangements at the distal end.
Figure 3E:
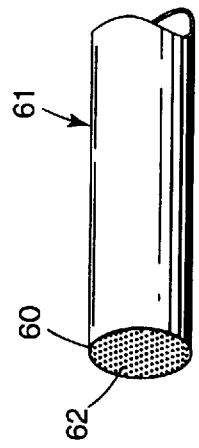
Figure 3A:
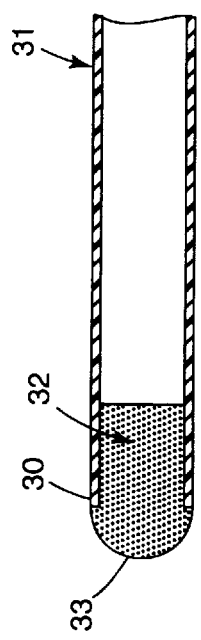
Figure 3B:
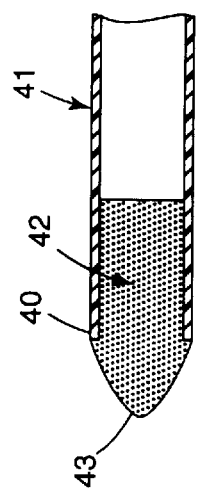
Figure 3C:
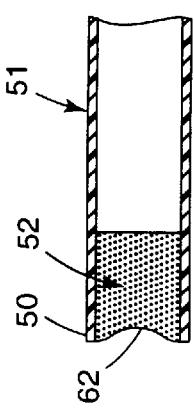

FIGS. 3a–3d illustrate four additional embodiments of a microbubble forming arrangement according to the invention. In FIG. 3a, the distal end 30 of hollow tube 31 includes a porous matrix 32 having a circular convex distal tip 33. In the embodiment of FIG. 3b, the distal end 40 of hollow tube 41 includes a porous matrix 42 having a non-circular convex distal end 43. In FIG. 3c, the distal end 50 of hollow tube 51 includes a porous matrix 52 having a concave distal end 53. FIG. 3d is a profile view of the distal end 60 of hollow tube 61 having a porous membrane 62 at the distal end of hollow tube 60. FIG. 3e is a perspective view of the distal end 60 of hollow tube 61 further illustrating the porous membrane 62 at the distal end 60 of hollow tube 61.

Figure 4:
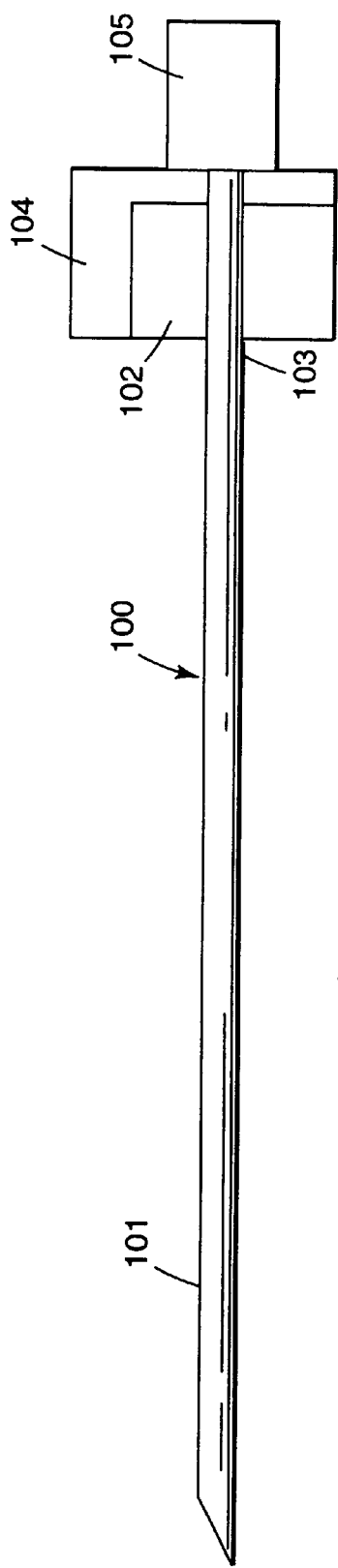
FIG. 4 illustrates a side view of an alternative embodiment of an apparatus for delivering microbubbles according to the invention.

FIG. 4 illustrates an alternative embodiment for formation of microbubbles in the vessel of a patient. According to this embodiment, a hollow tube 100 such as needle 101 includes a piezoelectric ultrasound transmitter 102 at the proximal end 103 of needle 101. A grip 104 surrounds piezoelectric transmitter 102 for holding the apparatus. A connecting mechanism 105 is at the proximal end 103 of needle 101 for connecting the apparatus to a gas source. Suitable connecting mechanisms, such as Luer® Lock, are known. In use, an inert gas, such as $CO_2$, can be passed into connecting mechanism 105 through needle 101. The ultrasonic waves formed by activation of piezoelectric ultrasound transmitter 102 causes a vibration that breaks the flow of the gas into microbubbles.

According to the method of the invention, a physiologically inert gas, such as $CO_2$, is used as an ultrasound contrast medium for imaging vessel wall structures and fluid flow through the vessels. When a gas such as $CO_2$ is injected into a blood vessel, the $CO_2$ will ultimately dissolve and be expired via the lung. The smaller the size of the microbubbles of $CO_2$, the faster the $CO_2$ will dissolve into the blood. The velocity of dissolving is a function of the surface area of the bubbles in the gas relative to the liquid. $CO_2$ is a preferred gas since it is a physiological gas with minimal side affects to the patient if given under certain volumes and pressures which are known. For example, administration of 200 ml of $CO_2$ per minute can easily be given to a human adult male or female without causing ischemia. Typically, the gas will be expired via the lung in two to three breaths.

Advantageously, detection of the gas in a patient using ultrasound equipment causes no ill effect to the patient's body. Moreover, ultrasound visualization is not harmful to the patient as compared to x-ray radiation used to image contrast agents such as iodine based agents.

Figure 5A:
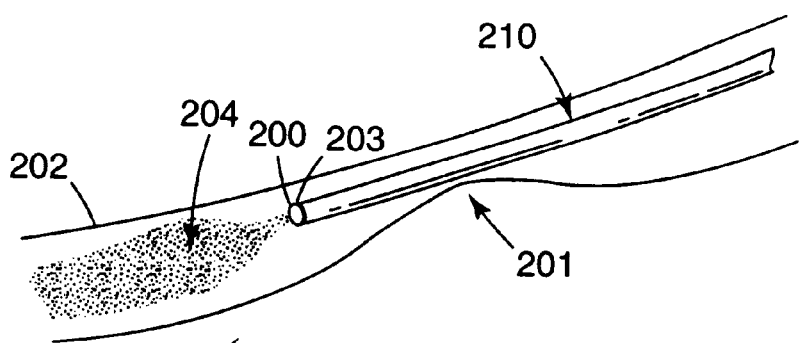
FIG. 5 illustrates the use of an apparatus according to the invention for detecting stenosis in a patient's blood vessel.
Figure 5B:
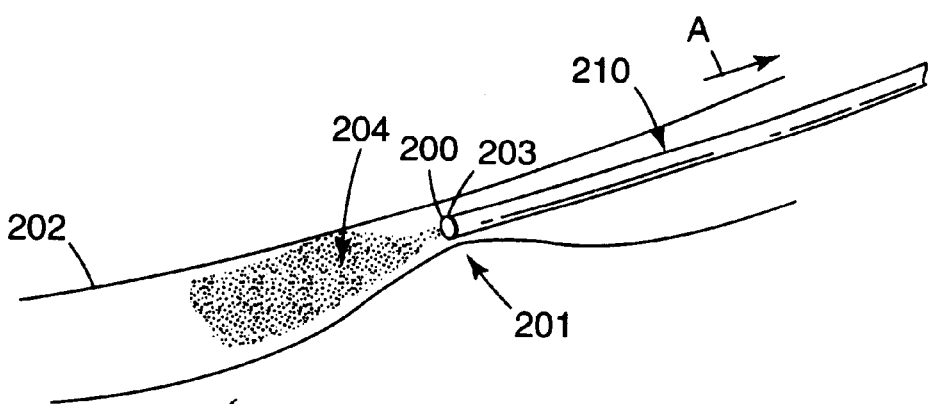
Figure 5C:
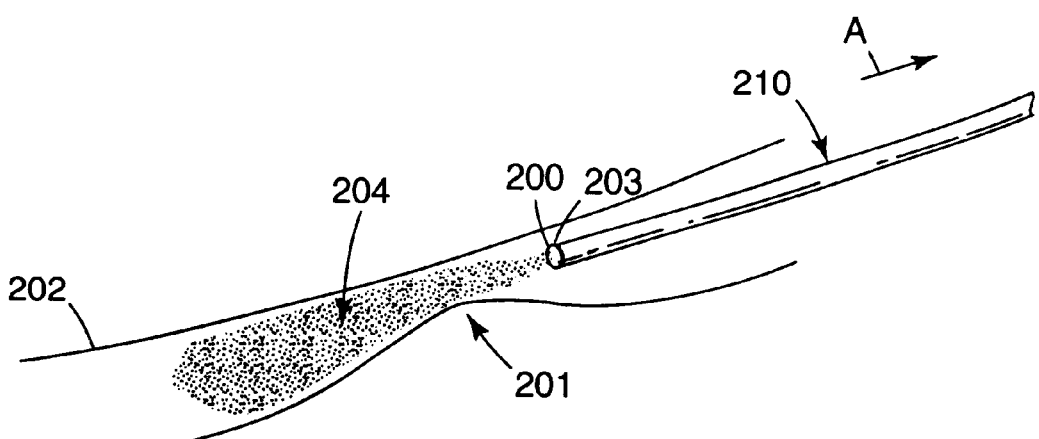

Referring to FIG. 5, a method of the invention for studying interior vascular contours will be described. In FIG. 5, the distal end 200 of catheter 210 is illustrated at a point distal to a region of stenosis 201. In FIG. 5a, microbubbles 204 are formed as a gas is passed from the proximal end (not shown) of catheter 210 through the microbubble forming arrangement 203 at the distal end 200 of catheter 210. The microbubbles can be detected by ultrasound imaging. FIGS. 5b and 5c sequentially illustrate proximal withdrawal (arrow A) of the distal end 200 of catheter 210 as the distal end 200 passes through, and proximal to (FIG. 5c), stenosis 201. Visualizing the microbubbles with ultrasound imaging as the catheter of 210 is passed through the stenotic area 201 permits the clinician to detect the stenosis 201. Typically, the flow pattern of microbubbles 204 is altered when passing through the stenotic region 201 of vessel 202. Due to the safety of $CO_2$ and ultrasound imaging, the clinician can repeatedly scan the region with no ill effects on a patient due to the contrast media or the diagnostic imaging instrumentation.

From the foregoing detailed description of the invention, it has been shown how the apparatuses and methods of the invention can be prepared and function in a preferred manner. However, modifications and equivalents of the disclosed concepts such as those that would occur to one of ordinary skill in the art, are intended to be included within the scope of the appended claims.

We claim:

1. An apparatus for delivering a contrast agent into a vessel comprising:

a tube having a lumen extending from a proximal end to a distal end of the tube; and a microbubble forming arrangement at the distal end of the lumen having microholes which cause formation of microbubbles when a gas is passed through the microbubble forming arrangement.

2. The apparatus according to claim 1, wherein the tube is a catheter.

3. The apparatus according to claim 1, wherein the tube is a needle.

4. The apparatus according to claim 1, wherein the microbubble forming arrangement is a porous matrix having microholes therethrough.

5. The apparatus according to claim 1, wherein the microbubble forming arrangement is a membrane having microholes therethrough.

6. The apparatus according to claim 4, wherein the porous matrix is of a material selected from the group comprising ceramic, sintered alloy, sintered nickel-titanium and sintered polytetrafluoroethylene.

7. A method for imaging an interior surface of a wall of a vessel, the method comprising a step of:

inserting an apparatus for delivering a contrast agent into the interior of the vessel, wherein the apparatus comprises:

(i) a tube having a lumen extending from a proximal end to a distal end of the tube; and (ii) a microbubble forming arrangement at the distal end of the lumen having microholes which cause formation of microbubbles when a gas is passed through the microbubble forming arrangement; and passing a gas through the microbubble forming arrangement at the distal end of the tube to form microbubbles within the interior of the vessel;

imaging the microbubbles passing along the interior surface of the vessel wall using an ultrasound imaging instrument.

8. The method according to claim 7, wherein the tube is a catheter.

9. The method according to claim 7, wherein the tube is a needle.

10. The method according to claim 7, wherein the microbubble forming arrangement is a porous matrix having microholes which form microbubbles when a gas is passed therethrough.

11. The method according to claim 7, wherein the microbubble forming arrangement is a membrane having microholes which form microbubbles when a gas is passed therethrough.

12. The method according to claim 10, wherein the porous matrix is of a material selected from the group comprising ceramic, sintered alloy, sintered nickel-titanium and sintered polytetrafluoroethylene.

13. The method according to claim 7 wherein the gas is $CO_2$.

14. The method according to claim 7 wherein the microbubbles formed are of a size of about 1 $\mu$m to 50 $\mu$m.

15. A method for delivering microbubbles to the interior of a vessel, the method comprising a step of:

inserting an apparatus for delivering a contrast agent into the interior of the vessel, wherein the apparatus comprises:

(i) a tube having a lumen extending from a proximal end to a distal end of the tube; and (ii) a microbubble forming arrangement at the distal end of the lumen having microholes which cause formation of microbubbles when a gas is passed through the cover medium;

passing a gas through the microbubble forming arrangement at the distal end of the tube to form microbubbles within the interior of the vessel.

16. The method according to claim 15 wherein the microbubbles are imaged with ultrasound imaging instrumentation as the microbubbles pass along the interior surface of the vessel wall.

17. The method according to claim 15 wherein a rate of flow of fluid passing through the vessel is measured by calculating the rate of flow of microbubbles that are passed into the interior of the vessel.

18. An apparatus for delivering a contrast agent into a vessel comprising:

a tube having a lumen extending from a proximal end to a distal end of the tube; and an arrangement for transmitting ultrasound waves to the proximal end of the tube that can create a vibration which causes formation of microbubbles to pass out the distal end of the tube when ultrasound waves are applied to a gas flowing through the tube.

* * * * *